(12) United States Patent
Waller

(10) Patent No.: US 8,945,062 B2
(45) Date of Patent: Feb. 3, 2015

(54) BARRIER SYSTEM TO REDUCE THE RATES OF LINE-RELATED INFECTIONS

(75) Inventor: Stephen Waller, Overland Park, KS (US)

(73) Assignee: Univeristy of Kansas, Lawrence, KS (US)

(*) Notice: Subject to any disclaimer, the term of this patent is extended or adjusted under 35 U.S.C. 154(b) by 0 days.

(21) Appl. No.: 12/334,056

(22) Filed: Dec. 12, 2008

(65) Prior Publication Data

US 2009/0157000 A1 Jun. 18, 2009

Related U.S. Application Data

(60) Provisional application No. 61/012,990, filed on Dec. 12, 2007.

(51) Int. Cl.
*A61M 5/32* (2006.01)
*A61M 5/14* (2006.01)
*A61M 25/02* (2006.01)
(Continued)

(52) U.S. Cl.
CPC ............ *A61M 5/1418* (2013.01); *A61M 25/02* (2013.01); *A61M 39/0247* (2013.01); *A61M 5/158* (2013.01); *A61M 2025/024* (2013.01); *A61M 2039/0261* (2013.01); *A61M 2039/0273* (2013.01); *A61M 2039/0294* (2013.01); *A61M 2039/0297* (2013.01)
USPC ........................................... 604/180; 604/174

(58) Field of Classification Search
CPC ............ A61M 39/0247; A61M 39/0294; A61M 39/0261; A61M 39/0273; A61M 39/0297; A61M 2025/0204; A61M 5/158; A61M 5/1418; A61M 25/02
USPC ................... 604/174, 180, 179, 389; 602/52
See application file for complete search history.

(56) References Cited

U.S. PATENT DOCUMENTS 3,487,837 A * 1/1970 Petersen ................... 604/180
4,360,025 A 11/1982 Edwards
(Continued)

FOREIGN PATENT DOCUMENTS

WO WO 2005046760 * 5/2005

OTHER PUBLICATIONS

Bhende, Shubhangi, In Vitro Assessment of Microbial Barrier Properties of Dermabond® Topical Skin Adhesive, Surgical Infections, 2002, pp. 251-257, vol. 3, No. 3, Mary Ann Liebert, Inc.
(Continued)

*Primary Examiner* — Matthew F Desanto
(74) *Attorney, Agent, or Firm* — Workman Nydegger

(57) ABSTRACT

A barrier system is provided for use in reducing infections associated with a percutaneous medical device, such as a catheter, that is disposed within a percutaneous incision. Such a barrier system can include: a barrier device having a skin-contacting surface and a catheter-receiving surface; and an adhesive composition configured for adhering to skin, the barrier device, and/or the catheter so as to form a barrier at or adjacent to an incision in the skin where the catheter is percutaneously inserted through the skin. The barrier device can include a conduit configured to receive the catheter. Alternatively, the barrier device can include a groove in a base surface that is configured to receive the catheter. A system that includes a medical device, the barrier device, and adhesive can also be provided.

25 Claims, 11 Drawing Sheets

(51) Int. Cl.
*A61M 39/02* (2006.01)
*A61M 5/158* (2006.01)

(56) References Cited

U.S. PATENT DOCUMENTS

| | | | | |
|---|---|---|---|---|
| 4,579,120 | A * | 4/1986 | MacGregor | 600/392 |
| 4,645,492 | A * | 2/1987 | Weeks | 604/174 |
| 4,767,411 | A | 8/1988 | Edmunds | |
| 4,915,694 | A | 4/1990 | Yamamoto et al. | |
| 5,019,096 | A | 5/1991 | Fox, Jr. et al. | |
| 5,308,338 | A | 5/1994 | Helfrich | |
| 5,685,859 | A | 11/1997 | Kornerup | |
| 5,807,341 | A * | 9/1998 | Heim | 604/174 |
| 5,833,665 | A | 11/1998 | Bootman et al. | |
| 5,918,983 | A * | 7/1999 | Palazzolo | 383/5 |
| 6,106,665 | A * | 8/2000 | Wood et al. | 156/379.6 |
| 6,132,399 | A | 10/2000 | Shultz | |
| 6,482,183 | B1 | 11/2002 | Pausch et al. | |
| 7,294,751 | B2 | 11/2007 | Propp et al. | |
| 7,354,421 | B2 | 4/2008 | Bierman | |
| 7,794,450 | B2 * | 9/2010 | Blott et al. | 604/543 |
| 2002/0038132 | A1 | 3/2002 | Abrams | 606/200 |
| 2005/0163827 | A1 * | 7/2005 | Zech et al. | 424/448 |
| 2005/0182443 | A1 | 8/2005 | John et al. | |
| 2007/0185441 | A1 | 8/2007 | Fangrow, Jr. | |
| 2008/0243082 | A1 * | 10/2008 | Goodman | 604/180 |
| 2008/0302365 | A1 * | 12/2008 | Cohen et al. | 128/206.12 |
| 2010/0100048 | A1 * | 4/2010 | Nielsen et al. | 604/173 |

OTHER PUBLICATIONS

Bierman S, Secret Refuge of the Microbial World; Infection Control Today: Clinical Update InfectionControlToday.com; Sep. 1, 2005; ICT.

Crnich, C and Maki, D. G.; The Promise of novel Technology for the Prevention of Intravascular Device-Related Bloodstream Infection. II. Long-Term Devices; Clinical Infectious Diseases; Article; Healthcare Epidemiology; May 15, 2002;pp. 1362-1368; vol. 34; Infectious Diseases Society of America.

Eiferman R & Snyder W.; Antibacterial Effect of Cyanoacrylate Glue; Arch Ophthalmol; Jun. 1983, pp. 958-960; vol. 101; University of Louisville.

Hadaway L.; infusing without infecting, Nursing2003, October, pp. 58-64, vol. 33, No. 10, www.nursingcenter.com.

Ho, K & Litton, E., Use of chlorhexidine-impregnated dressing to prevent vascular and epidural catheter colonization and infection: a meta-analysis, Journal of Antimicrobial Chemotherapy, Jun. 6, 2006, pp. 281-287, vol. 58, Oxford University Press on behalf of the British Society for Antimicrobial Chemotherapy.

Howell J, et al., Comparison of Effects of Suture and Cyanoacrylate Tissue Adhesive on Bacterial Counts in Contaminated Lacerations, Antimicrobial Agents and Chemotherapy, Feb. 1995, pp. 559-560, vol. 39, No. 2, American Society for Microbiology.

Levy, I, et al., Chlorhexidine-Impregnated Dressing for Prevention of Colonization of Central Venous Catheters in Infants and Children, The Pediatric Infectious Disease Journal, Original Studies, Aug. 2005, pp. 676-679, vol. 24, No. 8, Lippincott Williams & Wilkins.

Maki, D., et al., prevention of Central Venous Catheter-Related Bloodstream Infection by Use of an Antiseptic-Impregnated Catheter/A Randomized, Controlled Trial, Annals of Internal Medicine, Aug. 15, 1997, pp. 257-266, vol. 127, No. 4, American College of Physicians.

Mattick A, Use of tissue adhesives in the management of paediatric lacerations, Emerg Med J./Review, 2002, pp. 382-385, vol. 19, www.emjonline.com.

Nitsch A, et al., Cellular, Histomorphologic, and Clinical Characteristics of a New Octyl-2-Cyanoacrylate Skin Adhesive, Aesthetic Plastic Surgery, 2005, pp. 53-58, vol. 29, Springer Science + Business Media, Inc.

O'Grady, et al., Guidelines for the Prevention of Intravascular Catheter-Related Infections, Clinical Infectious Diseases/Article/Guidelines, Dec. 1, 2002, pp. 1281-1307, vol. 35.

Quinn, et al., Tissue Adhesive Versus Suture Wound Repair at 1 Year: Randomized Clinical Trial Correlating Early, 3-Month, and 1-Year Cosmetic Outcome, Annals of Emergency Medicine/Original Contribution, Dec. 1998, pp. 645-649, vol. 32, No. 6, American College of Emergency Physicians.

Rupp, M. et al. Effect of a Second-Generation Venous Catheter Impregnated with Chlorhexidine and Silver Sulfadiazine on Central Catheter-Related Infections/A Randomized, Controlled Trial, Annals of Internal Medicine/Article, Oct. 2005, pp. 570-581, vol. 143, No. 8, American College of Physicians.

Singer, A., et al., Comparison of wound-bursting strengths and surface characteristics of FDA-approved tissue adhesives for skin closure, J. Adhesion Sci. Technol., 2004, pp. 19-27, vol. 18, No. 1, VSP.

Singer, A., et al., Prospective, Randomized, Controlled Trial of Tissue Adhesive (2-Octylcyanoacrylate) vs Standard Wound Closure Techniques for Laceration Repair, Academic Emergency Medicine/ Scientific Advances, Feb. 1998, pp. 94-99, vol. 5, No. 2, Hospital of the University of Pennsylvania.

Yamamoto A, et al., Sutureless Securement Device Reduces Complications of Peripherally Inserted Central Venous Catheters, J Vasc Intery Radiol, 2002, pp. 77-81, vol. 13, No. 1, SCVIR, 2002.

* cited by examiner

BARRIER SYSTEM TO REDUCE THE RATES OF LINE-RELATED INFECTIONS

CROSS-REFERENCE TO RELATED APPLICATIONS

This patent application claims benefit of U.S. Patent Application Ser. No. 61/012,990, filed Dec. 12, 2007, which provisional application is incorporated herein by specific reference in its entirety.

BACKGROUND

Intravascular catheter infections have long plagued the medical community. These infections are typically caused by contamination of the catheter hub, with progression of the bacteria down the intraluminal surface of the catheter, and skin colonization, with progression of the bacterial down the extraluminal surface and into the bloodstream. Regarding the process, methods to reduce the number of catheter-related infections (CRI's) have included: strict insertion guidelines, the type of catheter material used, anti-microbial/antiseptic impregnated catheters, topical antibiotic ointments applied at the catheter insertion site and chlorhexidine impregnated sponges which encircle the catheter at the catheter-skin interface. These interventions have demonstrated varying degrees of efficacy. Despite these interventions, catheter infections still remain a problem.

Current barriers to catheter infections include antiseptics and antibiotics which have been applied to the entry site or embedded within the catheter itself. Though reductions in catheter-related infections have occurred with these interventions, these infections remain a problem and are associated with a concerning degree of morbidity and mortality and excess healthcare costs. Therefore, it would be beneficial to have an improved device and/or method of reducing catheter infection rates.

SUMMARY

In one embodiment, the present invention can include a barrier system for reducing infections associated with a catheter. Such a barrier system can include: a barrier device having a skin-contacting surface and a catheter-receiving surface; and an adhesive composition configured for adhering to skin, the barrier device, and/or the catheter so as to form a barrier at or adjacent to an incision in the skin where the catheter is percutaneously inserted through the skin. The barrier device can include a conduit configured to receive the catheter. Alternatively, the barrier device can include a groove in a base surface that is configured to receive the catheter.

In one embodiment, the adhesive can be a cyanoacrylate. For example, the cyanoacrylate can be ethyl-2-cyanoacrylate, and 2-octyl cyanoacrylate, or n-butyl-cyanoacrylate.

In one embodiment, the barrier device can include a base surface having a base opening that is in fluid communication with the conduit and an opposite surface having an opposite opening that is in fluid communication with the base opening via the conduit. Optionally, the conduit is substantially orthogonal with the base surface. Alternatively, the conduit is at an angle from about 0 degrees to about 90 degrees with respect to the base surface, or 10 to 80 degrees, 20 to 60 degrees, or about 45 degrees or more than or less than the stated degrees.

In one embodiment, the barrier system can include at least one of the following: a fastener disposed on the barrier device that is configured for receiving the catheter; one or more fastener straps on the barrier device that is configured to be affixed to the skin outward from the barrier device; a tapered base opening or opposite opening; a uniform conduit cross-sectional profile; a tapered conduit cross-sectional profile; a recess in the conduit configured for receiving the adhesive; a recess in the base surface configured for receiving the adhesive; a clam slit; a groove adjacent with the opposite opening; an o-ring; a suture cord; a chilling fluid conduit in the barrier device that communicates with a location for receiving the adhesive; an expandable bladder disposed on the barrier device; or a release cord disposed on the base surface of the barrier device.

In one embodiment, the barrier device can be disposed on the skin with the adhesive therebetween so as to receive the catheter protruding from the incision.

In one embodiment, the present invention can include a catheter system for reducing infections associated with catheters. Such a catheter system can include: a catheter medical device; a barrier device having a skin-contacting surface and a catheter-receiving surface; and an adhesive composition configured for adhering to skin, the barrier device, and/or the catheter so as to form a barrier at or adjacent to an incision in the skin where the catheter is percutaneously inserted through the skin. However, it should be recognized that the catheter can be substituted with any percutaneous medical device. The barrier device can be configured as any barrier device as described herein.

In one embodiment, the present invention can include a method for reducing infections associated with percutaneous medical devices. Such a method can include: inserting, percutaneously, a medical device into skin of a subject; applying an adhesive composition to the skin and a barrier device, said barrier device having a skin-contacting surface and a medical device-receiving surface; and adhering a barrier device to the skin with the adhesive composition so as to form an anti-microbial barrier with respect to the incision and medical device that inhibits microbes from infecting the incision. The method can also include applying the adhesive composition to the medical device so as to adhere the medical device to the barrier device and/or skin so as to form an anti-microbial barrier that inhibits microbes from infecting the incision. The adhesive can be applied onto at least one of the skin-contacting surface or medical device-contacting surface of the barrier device. For example, the adhesive can be applied to at least one of the following: a junction between the barrier device and skin; a junction between the barrier device, skin, and air; a junction between the barrier device and medical device; a junction between the barrier device, medical device, and air; or a junction between the barrier device, medical device, and skin.

These and other embodiments and features of the present invention will become more fully apparent from the following description and appended claims, or may be learned by the practice of the invention as set forth hereinafter.

DESCRIPTION OF FIGURES

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope (e.g., figures are not drawn to scale). The invention will be described and explained with additional specificity and detail through the use of the accompanying drawings in which.

DETAILED DESCRIPTION

Figure 1A:
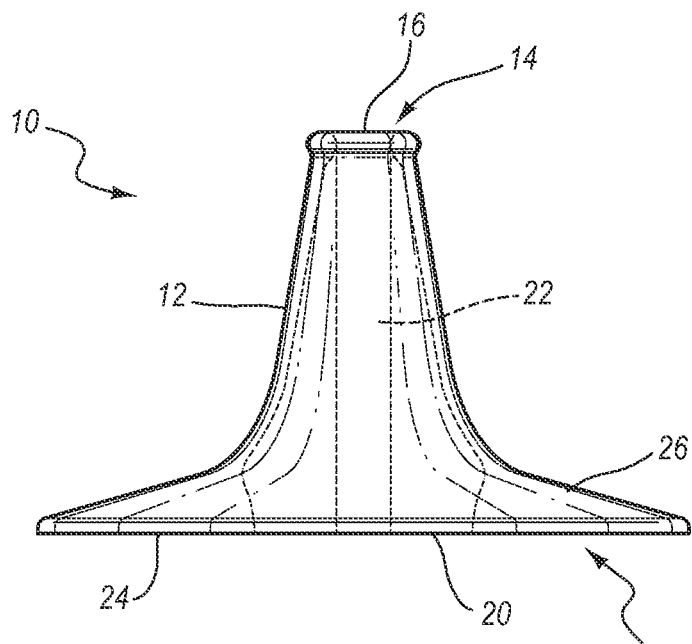
FIGS. 1A-1C include various views of an embodiment of a barrier device in accordance with the present invention.

Generally, the present invention includes a barrier device, adhesive composition, system having the device and adhesive, and methods of using the device and adhesive that inhibit and/or prevent infections from occurring at or in an insertion site where a medical device (e.g., catheter) penetrates the skin. For example, the insertion site can be from a catheter, needle, or other medical device that is inserted through the skin. Also, the barrier device and adhesive can be used to affix the medical device at a desired position with respect to the insertion site so that the medical device does not move during a medical procedure or during normal patient movement. Affixing the medical device at or in the insertion site can inhibit microbes from migrating into the insertion site by inhibiting the inward and outward slippage of the medical device with respect to the incision (e.g., pistoning). Thus, the device can be applied to skin at or proximal to an insertion site in the skin with the adhesive in order to inhibit and/or prevent infections from occurring and/or propagating at the insertion site.

The device and adhesive can cooperate so as to provide a mechanical barrier on the skin at the insertion site as well as adjacent to the insertion site. The design of the device and use of the adhesive can allow for the formation of one or more barrier points that can inhibit and/or prevent microbes from entering into the insertion site. Also, the device and adhesive combination can provide one or more anti-microbial barriers that can inhibit propagation of the microbes that come into contact with the medical device, skin, or the like. A barrier point is formed by adhering skin to the device and optionally adhering the skin and/or device to the medical device so as to occlude the insertion site. This inhibits microbes from entering into and infecting the insertion site.

The use of a device and adhesive can provide an impermeable barrier against the bacteria that tend to infect catheters by contaminating the catheter at the site of skin entry and subsequently traveling down the external surface of the catheter and into the bloodstream. Importantly, the device and adhesive can be used without the need for many of the antimicrobials and antiseptics that are commonly employed. Such a barrier can eliminate issues of organism resistance that are commonly associated with the currently available antimicrobials and antiseptics. Thus, the device and adhesive can be advantageous in limiting the use of antimicrobials and antiseptics, and thereby reduce the onset or occurrence of drug resistant microbes.

Current practices try to decrease the incidence of CRI by decreasing the bacterial load through antiseptics or antibiotics. However, CRI can now be inhibited or ameliorated by a method of using a composition and/or medical device as a barrier at a site where a medical device is inserted into skin. As such, the inventive composition and/or medical device can block access of the colonizing bacteria to the extraluminal surface of the catheter at the skin-catheter interface. Also, such a method of using the inventive composition and/or medical device can be used in addition to current infection-reducing interventions.

While the barrier device can be used in a manner that does not require the use of an antimicrobial composition, such antimicrobial compositions can be applied at various locations with respect to the barrier device and placement on the skin. For example, the antimicrobial composition, such as a traditional antibiotic or antiseptic (e.g., chlorhexidine, alcohols, quaternary ammonium compounds, boric acid, chlorhexidine gluconate, iodine, etc.) somewhere like reservoir. The antimicrobial composition can be placed in substantially any place the adhesive can be place. This can include the antimicrobial composition being deposited on a skin-contacting surface, medical device-contacting surface, or the like.

I. Barrier Device

The barrier device is configured to receive a percutaneous medical device and retain the medical device in a substantially fixed position with respect to the percutaneous incision. The barrier device is also configured to receive an adhesive so as to secure the barrier device to the skin proximal and/or around the incision, where the barrier device can receive the adhesive in one or more locations. The barrier device can have various configurations in order to achieve the functionalities described herein, which can include providing a barrier against contaminants and microbes as well as holding and retaining the medical device in a substantially fixed position such that the medical device does not move into and/or out of the incision during a medical procedure. This can prevent the slight wiggles or repositioning of the medical device that may lead to bacteria entering into the incision.

Additionally, the barrier device can be used to prevent movement of the medical device with respect to the incision during typical patient movement. In many instances, a medical device, such as a pin or rod used for bone alignment, can percutaneously extend through the skin for an extended duration of healing. During this time, the patient is likely to be ambulatory, which in itself can cause the medical device to shift or move into and/or out from the incision. The barrier device of the present invention can be utilized for such extended treatments to inhibit or prevent the medical device from moving in or out of the incision.

The barrier device can include a conduit or groove for receiving the medical device. In the instance of a conduit, the medical device can be slid through the conduit or groove before, during, or after insertion through the incision. In the instance of a groove, the barrier device can be applied or snapped onto the medical device after insertion through the incision; however, the barrier device can also be applied or snapped onto the medical device before or during placement into the incision. In another aspect, the barrier device can have an open (e.g., open clam) and closed position (e.g., closed clam), where the opened position allows for the medical device to be passed into an opened conduit before, during, or after insertion into the incision, and the barrier device can then be closed and sealed to provide a closed conduit. After the medical device and barrier device are properly placed as desired or needed, the adhesive can be applied to selected positions of the barrier device so as to adhere the barrier device to the skin and/or medical device. Optionally, the adhesive can be applied to the skin at or proximal to the incision before placement of the barrier device, or applied to the barrier device base before being placed on the skin.

The combination of the barrier device and adhesive can be configured so as to assist in maintaining the medical device (e.g., catheter) in a stable position with respect to the skin and incision, as well as providing a barrier to microbes to inhibit and/or prevent infections related to the percutaneous medical device. Besides catheters, the medical device can be any needle, external fixator pins (used to stabilize fractures of extremities that stick into bone and come out through the skin to an external stabilizing device) "K-wires" (small wires they typically run through finger joints to prevent severe skin contractures, after a burn, from permanently decreasing the range of motion of the fingers; these wires go through bone then exit the skin), and any other percutaneous medical device.

FIGS. 1A-1D provide an illustration of an embodiment of a barrier device 10. FIG. 1A shows that the barrier device 10 is formed from a body 12 that has a first end 14 with a first opening 16 that is opposite from a second end 18 with a second opening 20. The first opening 16 is in fluid communication with the second opening 20 via a substantially straight conduit 22. The body 12 is illustrated to have a tapered cross-sectional profile 28 from the first end 14 to the second end 18. However, the body 12 can have any shape that can provide the barrier/retention properties as described herein. As shown, the first end 14 has a smaller cross-sectional profile 28 compared to the second end 18. Accordingly, the second end 18 can include a base 24 that is configured for placement onto skin 40 such that the conduit 22 is aligned with a percutaneous incision 46. Also, the second end 18 is shown to have a flared portion 26 that provides stability to the device 10 during use. The tapered cross-sectional profile 28 can be tapered at a constant rate, or flared as illustrated.

Figure 1B:
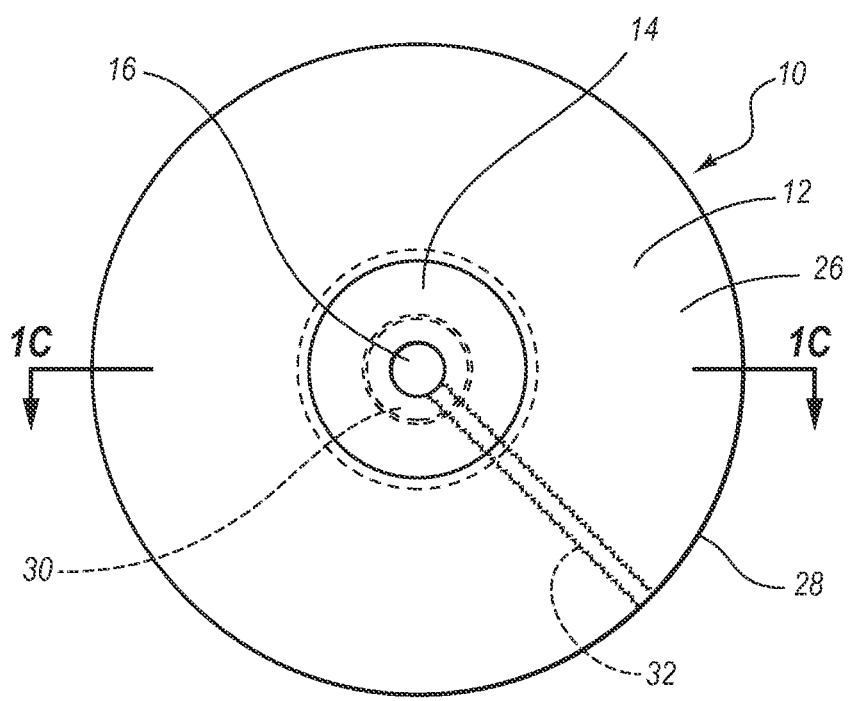

FIG. 1B shows a top view of the barrier device 10, which shows the cross-sectional profile 28 of the body 12 is substantially circular. However, the cross-sectional profile 28 can be any other possible shape, such as triangle, square, rectangle, pentagon, polygon, combinations thereof, and the like. Also, the cross-sectional profile 28 can change shapes from one portion to another portion of the device 10. The first opening 16 can include a taper 30 that narrows into the conduit 22 so that a medical device 48 is easily received therein.

While the body 12 can have a solid circular cross-sectional profile 28 and a closed conduit 22, the body 12 can optionally include a separating slit 32 extending from the first opening 16 to the second opening 20 so that the device 10 can open like a clam. By including a separating slit 32, the device 10 can be applied to a medical device 48 that is already inserted through a percuteneous incision. The configuration of the slit 32 can vary. For example, the slit 32 can include a cooperating junction, blunt end junction, matting junction, or the like. The adhesive that forms the barrier or other adhesive can be used to couple or integrate the sides of the slit 32 together.

Figure 1C:
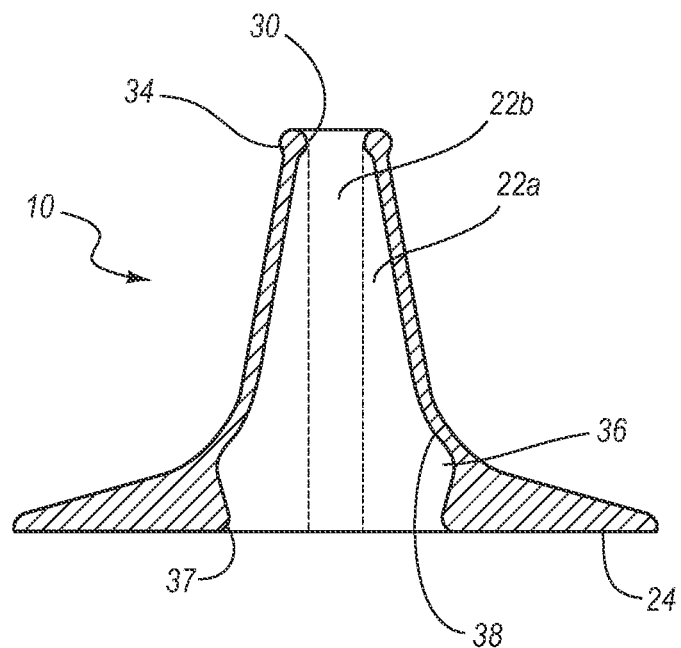

FIG. 1C shows a cutaway side view of the barrier device 10. This view shows the thickness of the body 12 with respect to the cross-sectional profile 28 at various locations along the device 10 or conduit. The first end 14 is shown to have first opening 16 that communicates with the conduit 22. The first opening 16 can include a taper 30 that narrows to the conduit 22 so that a medical device 48 can be passed therethrough and into the conduit 22 with ease. The conduit 22 can have a substantially uniform cross-sectional profile as shown by 22b, or the conduit 22 can have a tapered conduit as shown by 22a. While not shown, the conduit 22 can also have a widening conduit that is wider at the first opening 16 compared to the second opening 20. The thickness of the body 12 is dependent on the overall shape of the body 12 as well as the shape of the conduit 22.

The first end 14 is shown to have a thicker body portion at the lip 34 of the first opening 16. The lip 34 can provide increased structural integrity so that the barrier device 10 does not crack, split, or otherwise break during use or when the medical device 48 traverses through the conduit 22.

At the second end 18, the base 24 is shown to have a substantial surface area for contacting with the skin 40. This can provide the base 24 with substantial stability in contacting the skin and being retained in place, as desired or needed.

The conduit 22, while being uniform (22b) or tapered (22a) can also include recesses 36 or the like that can be used as reservoirs for the adhesive. The adhesive can be applied to the recess 36 so that the medical device can be adhered to a conduit surface 38. Also, the second opening 20 can include an expanded area, which can be formed from a tapered surface when entering the conduit 22 from the second opening 20. The expanded area can be configured for receiving adhesive in a location adjacent to the skin 40 so as to adhere the skin 40 to the medical device 48 and barrier 10 at locations around or adjacent to the incision 46.

Figure 1D:
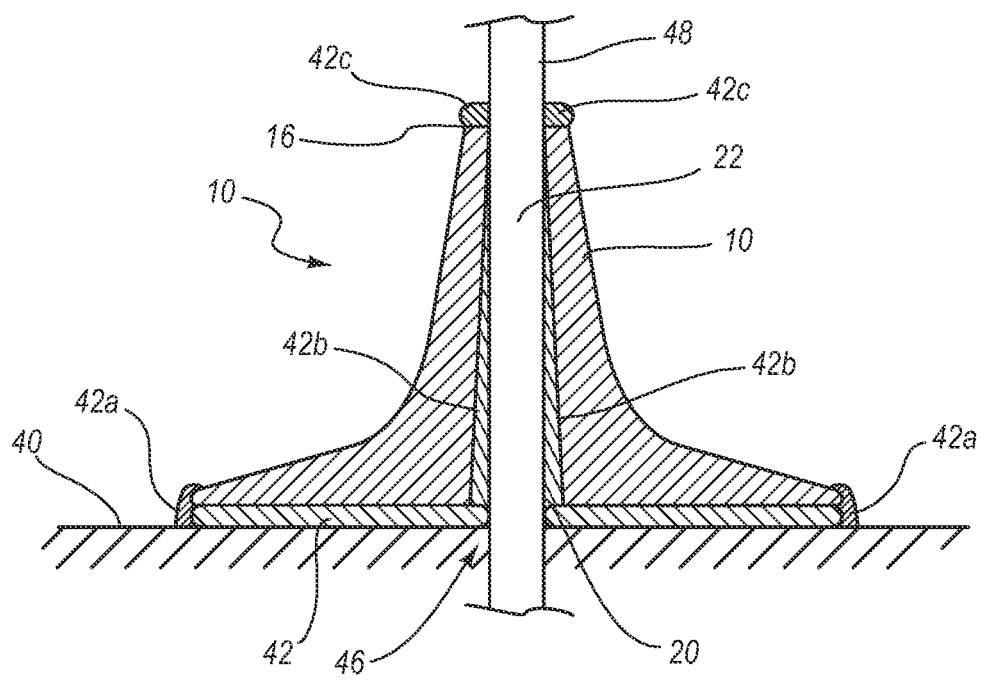
FIG. 1D includes an illustration of the barrier device of FIGS. 1A-1C during use.

FIG. 1D shows a cutaway side view of the device 10 illustrated in FIGS. 1A-1C during use. The device 10 is applied to the skin 40 and adhered thereto by having adhesive 42 applied to a portion, annular area, or entire base 24 of the device 10. Also, the adhesive 42a can be applied to the perimeter 44 of the base 24 to form an outer seal (42a). The device 10 is adhered to the skin 40 such that the conduit 22 is aligned with a percutaneous incision 46 that extends into tissue under the skin 40. This allows a medical device 48 (e.g., catheter) to be placed in the conduit 22 and into the incision 46.

Optionally, adhesive 42 can be placed in the conduit 22 to form a conduit seal 42b, on the first opening 16 to form a first opening seal 42c, on the second opening 20 to form a second opening seal 42d, or the like. The adhesive 42 can be applied to any location on the device 10 that is in contact with skin 40 and/or the medical device 48.

FIGS. 2A-2D illustrate another embodiment of a barrier device 50 that has many features in common with the barrier device 10 of FIGS. 1A-1D. The barrier device 50 is formed from a body 52 that has a base member 54 with a base opening 56 that is coupled to an elongate, bent tube 58 with a tube opening 60. The base opening 56 is in fluid communication with the tube opening 60 via a bent conduit 62. As shown, the base member 54 has a substantially constant cross-sectional profile 68, and is coupled to the tube 58, which has a varying cross-sectional profile 68. The base member 54 and the tube 58 can be a uniform member or two separate members that are coupled together. The base member 54 can include a base surface 64 that is configured for placement onto skin such that the conduit 62 is aligned with a percutaneous incision 46.

Figure 2A:
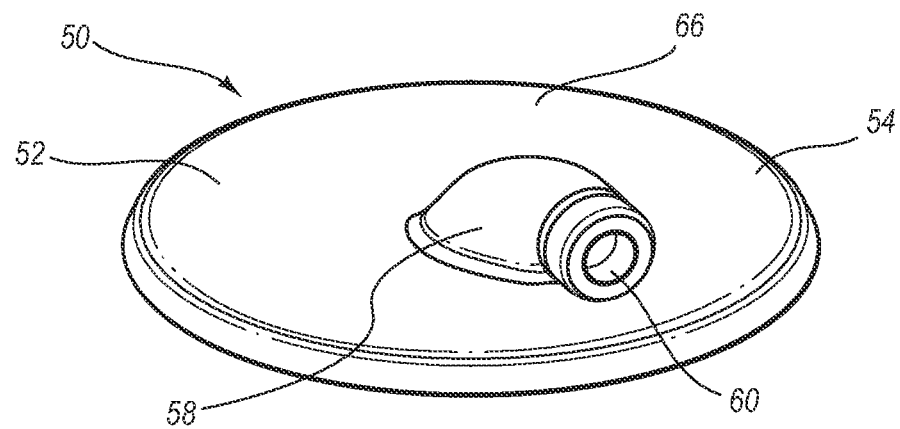
FIGS. 2A-2C include various views of an embodiment of a barrier device in accordance with the present invention.
Figure 2B:
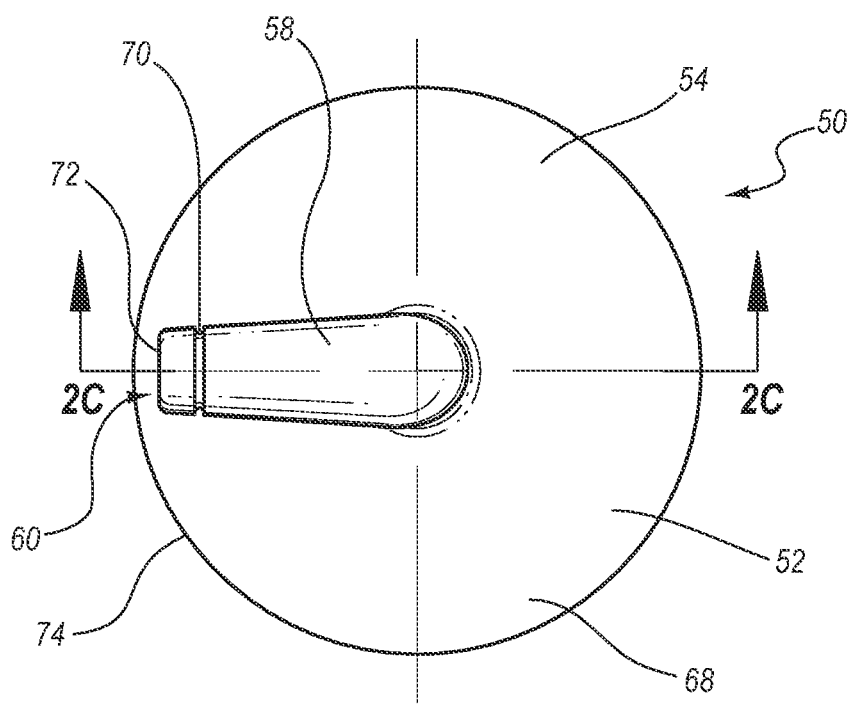

FIG. 2B shows a top view of the barrier device 50, which shows the cross-sectional profile 68 of the body 52 is substantially circular. However, the cross-sectional profile 68 can be any other possible shape, such as triangle, square, rectangle, pentagon, polygon, combinations thereof, and the like. The tube 58 is shown to be positioned such that the tube opening 60 is directed laterally from the base member 54. Also, the tube 58 is shown to include a circumferential groove 70 that is configured to receive a fastener member (not shown) of a medical device. For example, the medical device can include an annular protrusion that aligns with the groove 70 so at to mate and fasten the device 50 with the medical device. Alternative, the groove 70 can receive a restricting member (not shown) such as an o-ring, suture, or the like that can contract and constrict the tube 58 so that the conduit 62 grabs the medical device so inhibit movement therebetween. In another alternative, the groove 70 can be used to receive adhesive so as to form a seal at the tube opening 60 with the medical device 48. Also, the groove 70 can be used to receive a suture to increase security of the medical device with respect to the barrier device 50.

While the tube end 72 is shown to terminate before reaching the outer perimeter 74 of the base member 54, the tube end 72 can extend past or be the terminate at the outer perimeter 74 of the base member 54. The base member 54 and tube 58 can include a openable slit (not shown) such that the device 50 can open up like a clam in order to receive the medical device into the conduit 62.

Figure 2C:
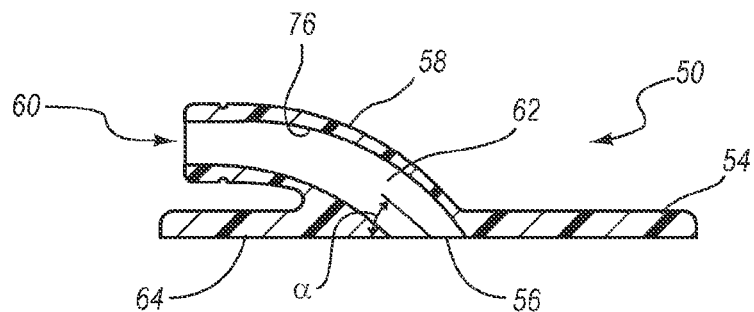

FIG. 2C shows a cutaway side view of the barrier device 50. This view shows the thickness of the body 52 with respect to the cross-sectional profile 68 at various locations along the device 50 or conduit 62. The base member 54 is shown to have base opening 56 that communicates with the conduit 62. The base opening 56 is shown to have an offset opening that is at an angle alpha with respect to the base surface 64, which would also be at an angle with respect to the skin 40 and tube 58. The conduit 62 can have a substantially uniform cross-sectional profile 68, or the conduit 62 can have a tapered conduit, or a shape that conforms with the external surface 66 of the device 10. The thickness of the body 52 is dependent on the overall shape of the body 52 as well as the shape of the conduit 62.

The base surface 64 is shown to have a substantial surface area for contacting with the skin 40. This can provide the base member 54 with substantial stability in contacting the skin 40 and being retained in place, as desired or needed.

While not shown, the conduit 62 can include recesses, expanded openings, or the like that can be used as reservoirs for the adhesive. The adhesive can be applied to the recess so that the medical device can be adhered to a conduit surface 76. The base member 54 and/or body 52 can also include recesses to be used as reservoirs for receiving the adhesive and affixation to the skin.

Figure 2D:
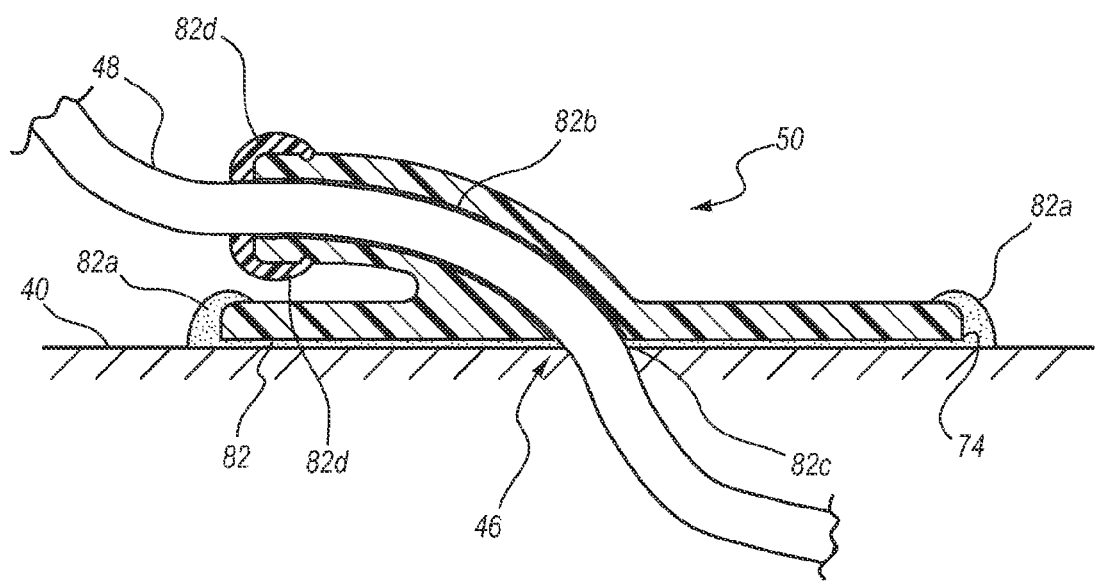
FIG. 2D includes an illustration of the barrier device of FIGS. 2A-2C during use.

FIG. 2D shows a cutaway side view of the device 50 illustrated in FIGS. 2A-2C during use. The device 50 is applied to the skin 40 and adhered thereto by having adhesive 82 applied to a portion, annular area, or entire base 64 of the device 50. Also, the adhesive 82a can be applied to the perimeter 74 of the base 54 to form an outer seal (82a). The device 50 is adhered to the skin 40 such that the conduit 62 is aligned with a percutaneous incision 46 that extends into tissue under the skin 40. This allows a medical device 48 (e.g., catheter) to be placed in the conduit 62 and into the incision 46.

Optionally, adhesive 82 can be placed in the conduit 62 to form a conduit seal 82b, on the base opening 56 to form a base opening seal 82c, on the tube opening 60 to form a tube opening seal 82d, or the like. The adhesive 42 can be applied to any location on the device 50 that is in contact with skin 40 and/or the medical device 48.

Figure 3A:
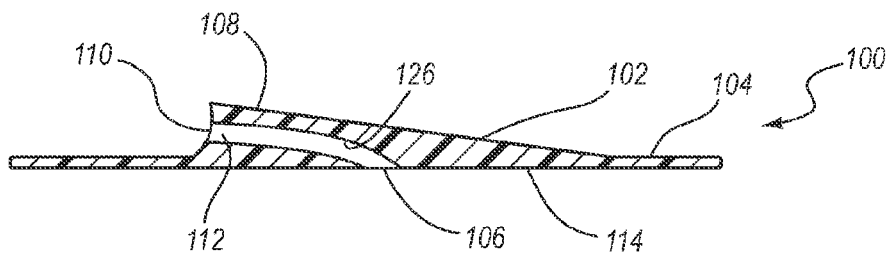
FIGS. 3A-3C include various views of an embodiment of a barrier device in accordance with the present invention.
Figure 3B:
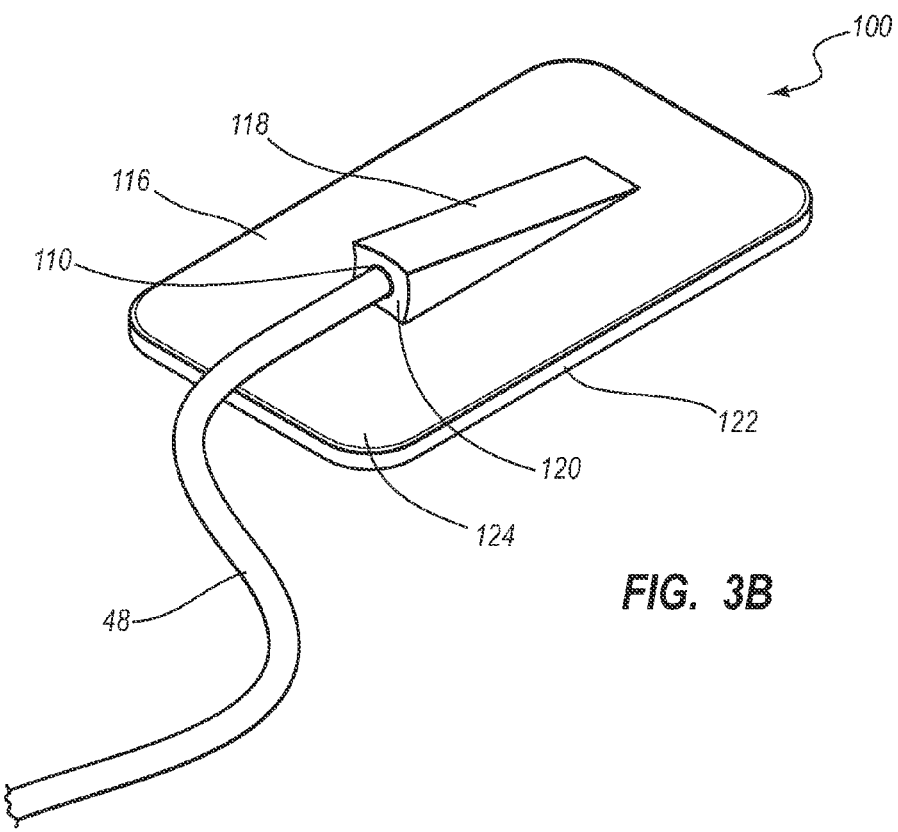
Figure 3C:
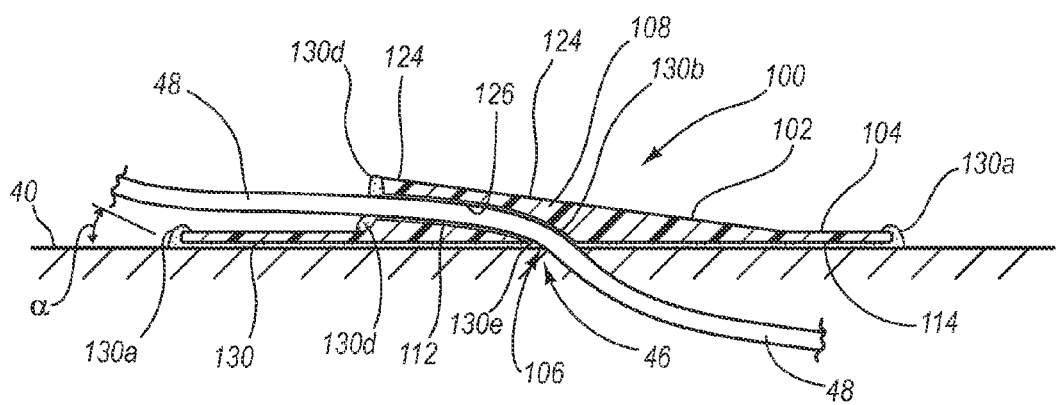

FIGS. 3A-3C illustrate another embodiment of a barrier device 100 that has many features in common with the barrier device 10 of FIGS. 1A-1D or device 50 of FIGS. 2A-2D. The barrier device 100 is formed from a body 102 that has a base member 104 with a base opening 106 that is coupled to a top member 108 with a top opening 110. The base opening 106 is in fluid communication with the top opening 110 via a conduit 112. As shown, the base member 104 has a substantially constant cross-sectional profile 116, and is coupled to the top member 108, which can have any cross-sectional profile 118. The base member 104 and the top member 108 can be a uniform member or two separate members that are coupled together. The base member 104 can include a base surface 114 that is configured for placement onto skin 40 such that the conduit 112 is aligned with a percutaneous incision 46.

FIG. 3B shows a top view of the barrier device 100, which shows the cross-sectional profile 116 of the base member 104 is substantially rectangular. However, the cross-sectional profile can be any other possible shape, such as triangle, square, circle, pentagon, polygon, combinations thereof, and the like. Similarly, the cross-sectional profile 118 of the top member 108 can be any shape, such as those described. The top member 108 is shown to be positioned such that the top opening 110 is directed laterally from the base member 104. Also, the top member 108 is shown to include a concave face 120, however, the face 120 can be blunt, convex or the like. The concave face 120 can aid in inserting the medical device into the conduit 112.

While the face 120 of the top member 108 is shown to terminate before reaching the outer perimeter 122 of the base member 104, the face 120 can extend past or be the terminate at the outer perimeter 122 of the base member 104. The base member 104 and top member 108 can include a openable slit (not shown) such that the device 100 can open and close like a clam in order to receive the medical device into the conduit 112.

FIG. 3C shows a cutaway side view of the barrier device 100 in use. This view shows the thickness of the body 102 with respect to the cross-sectional profile 116, 118 at various locations along the device 100 or conduit 112. The base member 104 is shown to have base opening 106 that communicates with the conduit 112. The base opening 106 is shown to have an offset opening that is at an angle alpha with respect to the base surface 114, which would also be at an angle with respect to the skin 40 and top member 108. The conduit 112 can have a substantially uniform cross-sectional profile, or the conduit 112 can have a tapered profile, or a shape that conforms with the external surface 124 of the device 10. The thickness of the body 102 is dependent on the overall shape of the body 102 as well as the shape of the conduit 112.

The base surface 114 is shown to have a substantial surface area for contacting with the skin 40. This can provide the base member 104 with substantial stability in contacting the skin 40 and being retained in place, as desired or needed. However, a base surface 114 having a minimal surface area could also be used to provide a barrier.

While not shown, the conduit 112 can include recesses, expanded openings, or the like that can be used as reservoirs for the adhesive. The adhesive can be applied to the recess so that the medical device can be adhered to a conduit surface 126.

The device 100 is applied to the skin 40 and adhered thereto by having adhesive 130 applied to a portion, annular area, or entire base surface 114 of the device 100. Also, the adhesive 130a can be applied to the perimeter 122 of the base 104 to form an outer seal (130a). The device 100 is adhered to the skin 40 such that the conduit 112 is aligned with a percutaneous incision 46 that extends into tissue under the skin 40. This allows a medical device 48 (e.g., catheter) to be placed in the conduit 112 and into the incision 46.

Optionally, adhesive 130 can be placed in the conduit 112 to form a conduit seal 130b, on the base opening 106 to form a base opening seal 130c, on the top opening 110 to form a top opening seal 130d, or the like. The adhesive 130 can be applied to any location on the device 100 that is in contact with skin 40 and/or the medical device 48.

Figure 4A:
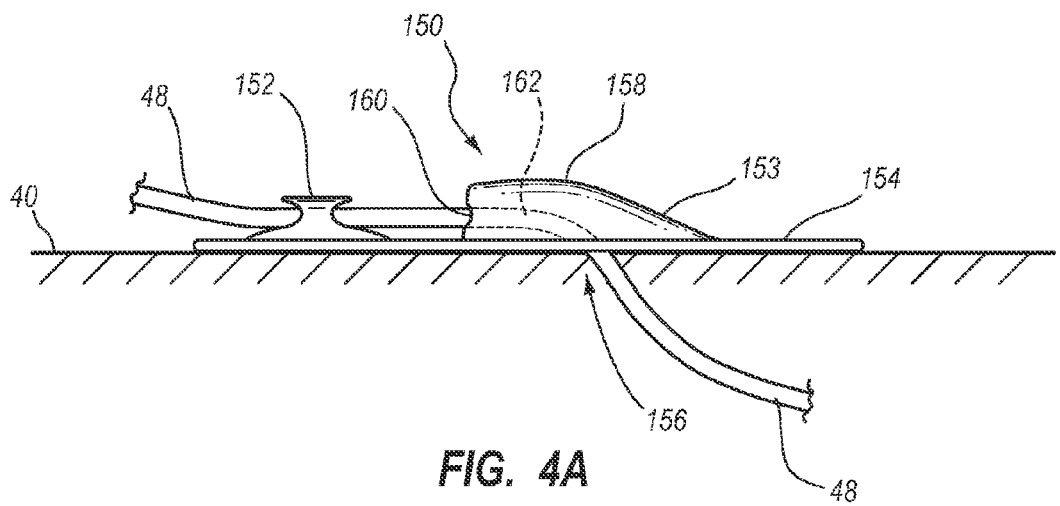
FIGS. 4A-4E include various views of an embodiment of a barrier device that includes a fastener, and also show different embodiments of fasteners for fastening a medical device to the barrier device.
Figure 4B:
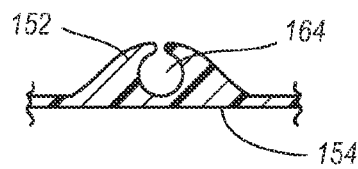

FIGS. 4A-4B illustrate another embodiment of a barrier device 150 that has many features in common with the barrier device 10 of FIGS. 1A-1D, device 50 of FIGS. 2A-2D, and device 100 of FIGS. 3A-3C. As illustrated, the barrier device 150 is configured substantially the same as the device of FIGS. 3A-3C; however, the features of FIGS. 4A-4B can also be applied to any barrier device described herein, and vice versa. The barrier device 150 is shown to include a fastener 152 that fastens the medical device 48 to the barrier device 150. The fastener 152 is advantageous in retaining the tube of the medical device 48 against the barrier device 150, which can aid in the retention and barrier properties of the device 150. Briefly, the barrier device 150 is formed from a body 153 that has a base member 154 with a base opening 156 that is coupled to a top member 158 with a top opening 160. The base opening 156 is in fluid communication with the top opening 160 via a conduit 162.

The fastener 152 is disposed on the base member 154 in a position that allows for receiving the medical device 48. The fastener 152 is configured similarly to a "C" clamp that can be manually opened by hand to receive the medical device 48. For example, the medical device 48 can be snapped into the fastener 152 so as to be received into the fastener receiver 164. The medical device 48 can then be removed from the fastener 152 by snapping the medical device 48 from the receiver 164, which can be done by hand.

Figure 4C:
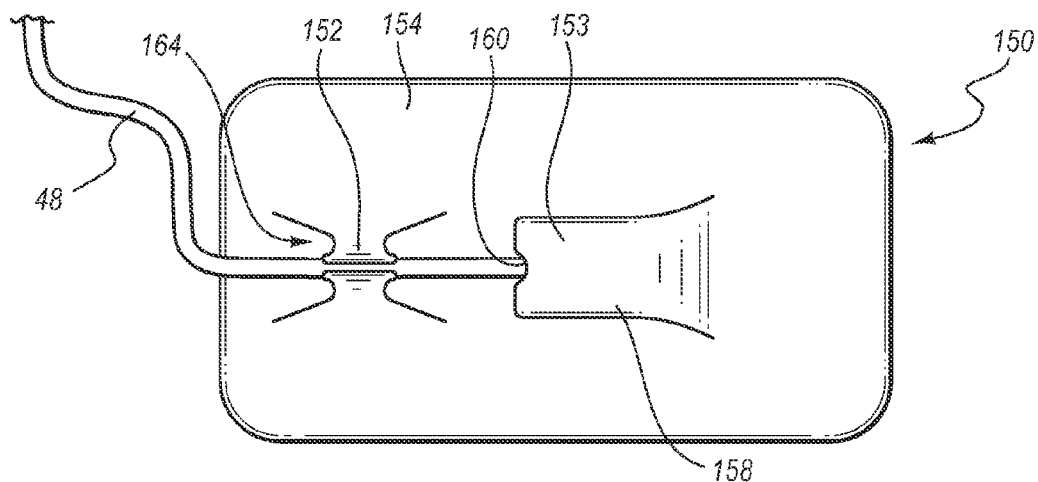
Figure 4D:
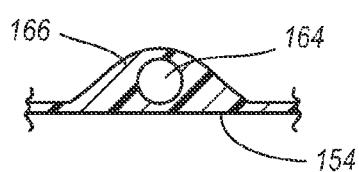
Figure 4E:
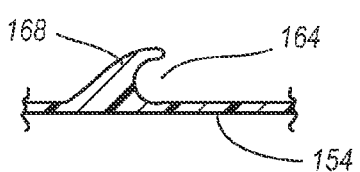

While the fastener 152 is shown to be in a "C" clamp configuration in FIG. 4A-4C, other types of fasteners can be employed, which can include a conduit fastener 166 (FIG. 4D), half fastener 168 (FIG. 4E), or the like. In fact, any suitable type of fastening system, such as those that are removable, releasable, flexible, elastic, and the like can be used with the barrier device.

Figure 5A:
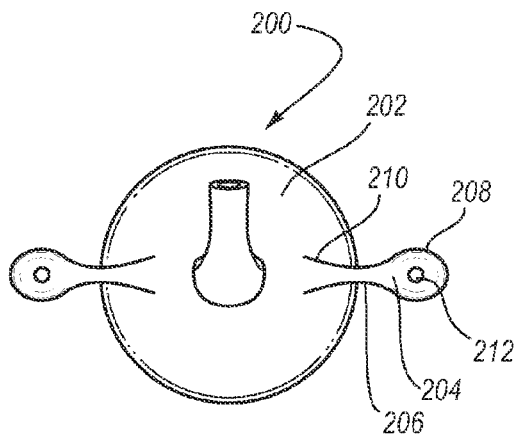
FIGS. 5A-5B include various views of an embodiment of a barrier device that includes securement straps.
Figure 5B:
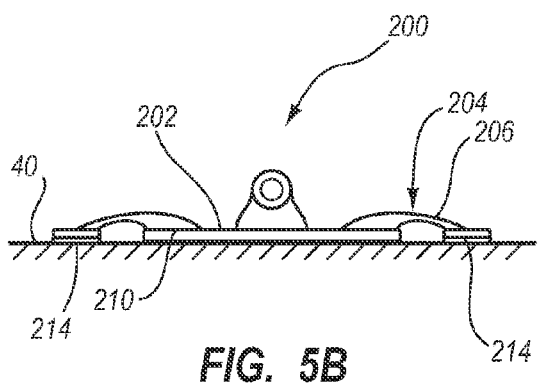

FIGS. 5A-5B illustrate another embodiment of a barrier device 200 that has many features in common with the device 50 of FIGS. 2A-2D. However, the features of FIGS. 5A-5B can also be applied to any barrier device described herein, and vice versa. As shown, the barrier device includes a base 202 configured as described herein. The base 202 includes one or more fastener straps 204 that extend from the base 202 so as to be disposed over the skin 40 when applied to a subject. The device 200 is shown to have two fastener straps 204; however, more or less straps 204 can be used. Each strap 204 can include a body 206 that has a terminal head 208 that can be disposed on the skin 40. the body 206 can be connected to the base 202 at a connection point 210, which can be rigid, flexible, stretchable, or the like. The strap 204 can be prepared from a uniform material with the base 202, or can be two separate members that are coupled together. The head 208 can be solid or have a hole 212. The head 208 can be configured for being affixed to the skin 40 in a fixed or removable manner. For example, the head 208 can be glued to the skin 40 with adhesive 214 (as shown) or sutured to the skin 40 with sutures (not shown). Other means of affixation can also be used. The straps 204 can improve the retention of the barrier device 200 to the skin 40. While the straps 204 are shown to have a defined shape, other shapes and configurations can be used so at to increase the retention of the barrier device 200 on the skin 40 so that it does not move during the medical procedure.

The barrier device can be prepared from any medically acceptable material. That is, any material that is used for a medical device, ranging from catheters to bandages, can be used in preparing a boot as described and shown herein. For example, the boot, which can be in various shapes and sizes, can be prepared from rubbers, elastomers, bandage-like materials, cloths, fibrous materials, paper, porous materials, plastics, hard plastics, maleable plastics, polyethylenes, polystyrenes, foams, memory foams, polyurethanes, latexes, and the like.

In one embodiment, the barrier device does not have an aperture or closed conduit, but can be configured to lay over a percutaneous medical device. The barrier device can have a receiving surface or recess that can receive the medical device. For example, the recess can be a semi-circular conduit that lays over the medical device and on the skin. As such, the barrier device can have a medical device receiving surface, groove, recess, or the like that can be flat, flexible, bendable, malleable, grooved so as to receive a catheter, and the like.

Figure 6A:
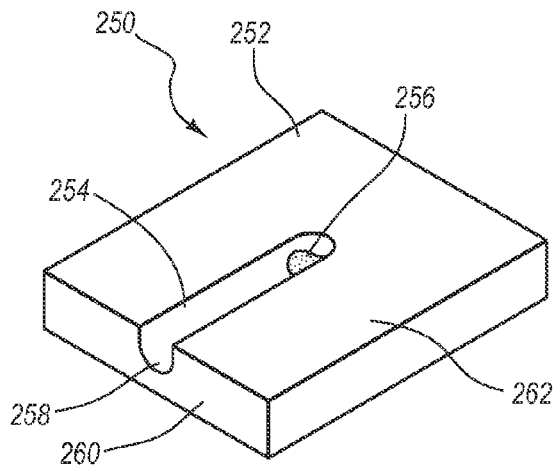
FIGS. 6A-6C include various views of an embodiment of a barrier device that has a medical device-receiving groove in a base surface.
Figure 6B:
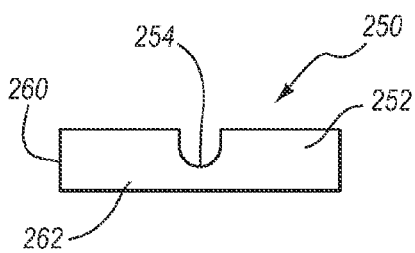
Figure 6C:
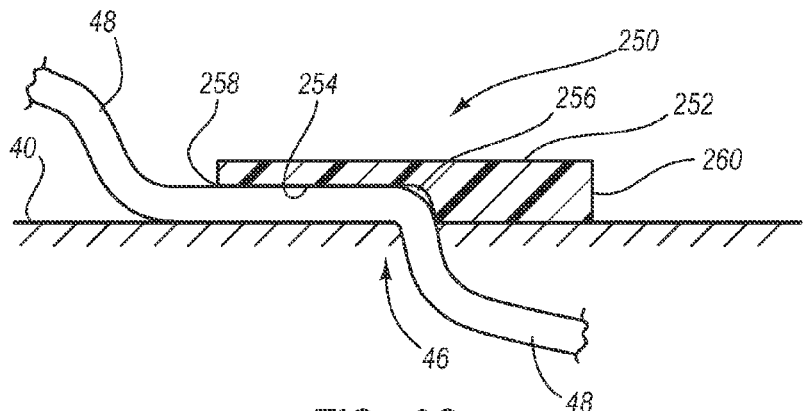

FIGS. 6A-6B show an embodiment of a barrier device 250 that includes a body 252 having a recess 254 configured for receiving a medical device 48. The recess 254 can have a closed end 256 that is located within the body 252. The closed end 256 can be configured for receiving the portion of the medical device 48 that protrudes from the percutaneous incision 46 in the skin 40. At the other end of the recess 254 is an open end 256 that opens from the device 250 so that the medical device can extend past the perimeter 260 of the device 250. The adhesive (not shown) can be applied to any portion of the device as described herein, including at any point on the recess 254 or perimeter 260 or base 262 of the body 252.

Figure 7A:
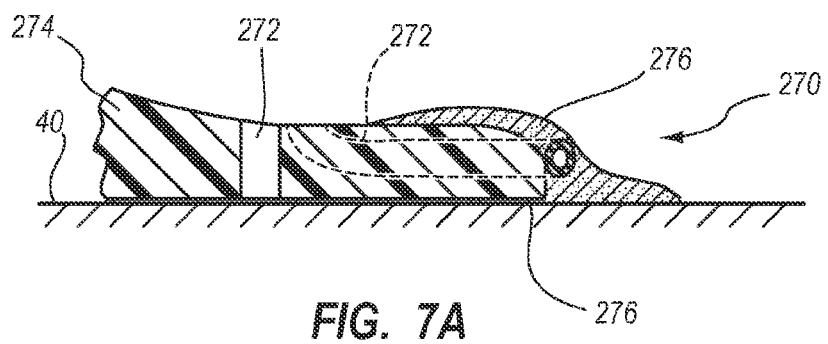
FIGS. 7A-7B include various views of an embodiment of a barrier device that includes chilling conduits.
Figure 7B:
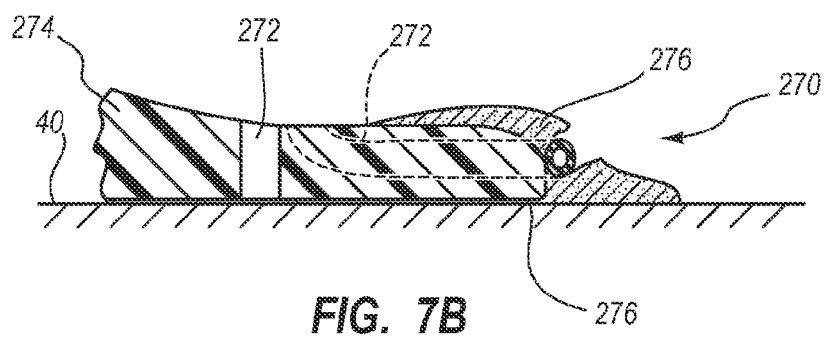

As shown in FIGS. 7A-7B, an embodiment of a barrier device 270 can include one or more chilling conduits 272 formed in the portion of the body 274 that contacts the skin. The chilling conduits 272 can be the same or different from the conduits described herein for receiving the medical device. The chilling conduits 272 are configured for receiving a chilled fluid that can be applied through the conduits 272 so as to provide the chilled fluid to the adhesive 276. Chilling can cause the adhesive 276 to become brittle and easily broken and/or separated from the skin. Suitable chilling fluids can include dimethyl ether, propane, liquid nitrogen, tetrafluoroethane, and the like. The use of chilling fluids can aid in removal of the device 270 when it is time to remove the medical device from the incision.

While chilling conduits are illustrated, such chilling conduits can be present in various sizes and configurations. The chilling conduit can be at any of the following: at a perimeter edge of the barrier device; around the perimeter of the barrier device; at the base of the barrier device; around the medical device conduit; around the top opening from which the medical device protrudes; in fluid communication with the medical device conduit; a conduit in communication with one or more of the foregoing conduits; combinations thereof; and the like. Additionally, components for introducing a chilling fluid into the chilling conduits can be included in the present invention, such as reservoirs of chilling fluids, tubing, tube fittings, syringes, and the like.

In one embodiment, the conduits, such as chilling conduit or medical device conduit, can include linings. As such, another material such as a polymer, metal, alloy, ceramic, fiberglass, or the like can be coated along the surface of the conduit to provide various properties. Such linings can be advantageous in providing structural integrity or for increasing the heat (cold) transfer characteristics for more rapid temperature changes.

In one embodiment, the chilling conduit can be filled within another material to change the properties of the barrier device. For example, the conduits can be filled with other polymers, metals, alloys, fiberglass, fiber optics, or the like. A metal-filled conduit can be used to provide cooler temperatures to the adhesives located on the other end of the conduit to increase the cooling of the adhesive. Metal conduits can also be used to propagate electricity across the adhesive to degrade adhesives that are subject to degradation when exposed to electrical currents. Also, a fiber optic-filled conduit, or other wave-guide or wave carrier, can be useful when the adhesive is subject to degradation upon receiving laser light or other energetic waves that can weaken the adhesive.

Figure 8A:
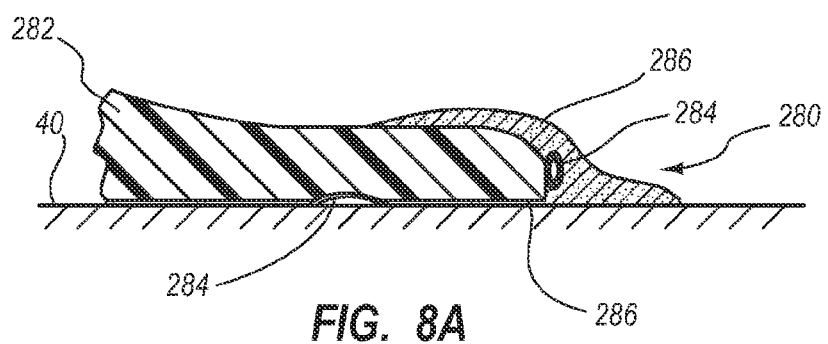
FIGS. 8A-8B include various views of an embodiment of a barrier device that includes an expandable bladder.
Figure 8B:
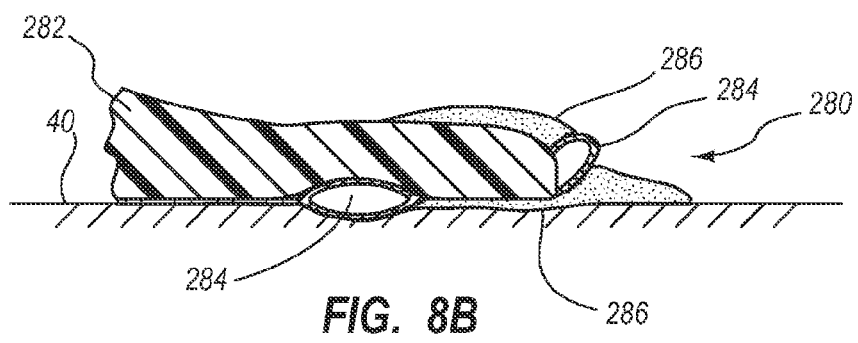

As shown in FIGS. 8A-8B, an embodiment of a barrier device 280 can include one or more expandable bladders 284 at locations on the body 282 of the barrier device 280 that contact the skin. During use, the bladders 284 can be in unexpanded states, and when the it is time for the medical device to be withdrawn, the bladders 284 can be expanded. Such an expansion can break the seal of the adhesive 286 so that the barrier device 280 can be easily removed from the skin. For example, the bladder 284 can be disposed on the base surface 288 of the body 282. While not shown, the body can also include conduits for passing gasses to the bladder 284 to enable inflation. Also, hypodermic needles or the like can be used to supply gasses to the bladder 284 to effect expansion.

Figure 9:
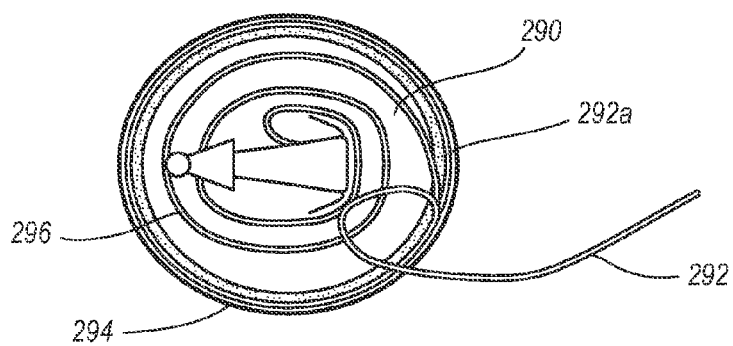
FIG. 9 includes an embodiment of a barrier device that includes a release cord.

FIG. 9 illustrates an embodiment of a barrier device 290 that can include a release cord 292. While shows to be located at the outer perimeter 294 of the device 290, the release cord 292 can be disposed anywhere on the device 40 that contacts the skin. For example, the release cord 292 can be in a coil formation 296 that coils along the base surface of the device. When it is time to remove the medical device from the incision, the release cord 292 can be pulled so as to break the seal and barrier between the barrier device 290 and the skin.

Figure 10A:
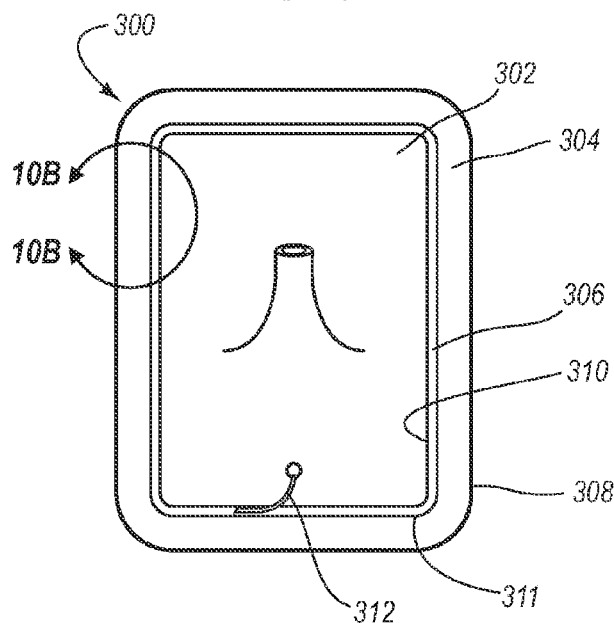
FIGS. 10A-10C include various views of an embodiment of a modular barrier device that includes decouplable members that can be separated by pulling a release wire.
Figure 10B:
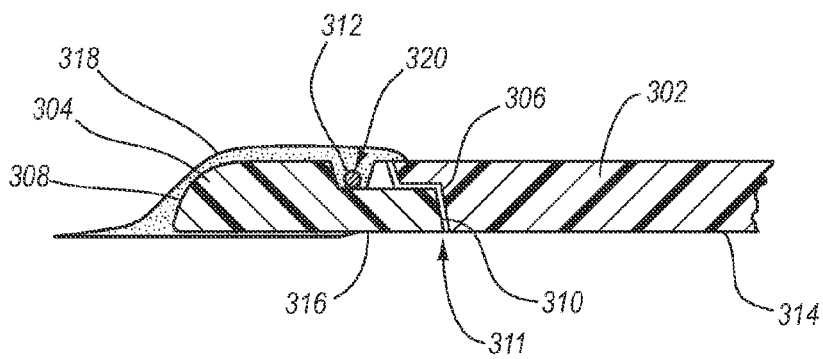
Figure 10C:
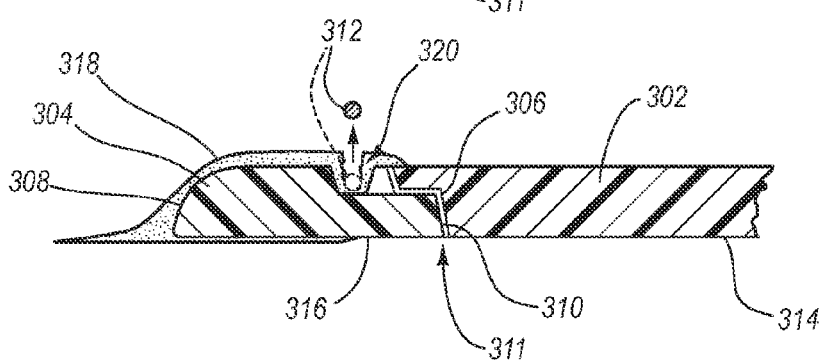

FIGS. 10A-10C illustrate an embodiment of a modular barrier device 300. The modular barrier device 300 can include a main barrier 302 and a perimeter barrier 304. The main barrier 302 can be configured as any barrier device as described herein. The perimeter barrier 304 is sized so as to be coupled/couplable to the perimeter surface 306 of the main barrier 302. For example, the perimeter barrier 304 can include an outer perimeter surface 308 and an inner perimeter surface 310 that is shaped and sized to conform with the perimeter surface 306 of the main barrier 302. When the main barrier 302 and perimeter barrier 304 are placed together so as to form the modular barrier device 300, the perimeter surface 306 forms a gap 311 with the inner perimeter surface 310 of the perimeter barrier 304. A wire 312 can be imbedded on, within, at, or adjacent to the gap 311, such that pulling the wire 312 allows for the main barrier 302 to be decoupled from the perimeter barrier 304. As shown, the wire 312 is disposed within a wire recess 320 that extends around inner perimeter surface 310 of the perimeter barrier 304; however, the wire 312 and wire recess 320 can be in or at the gap 311 as well as within the main barrier 302 proximal or adjacent to the perimeter surface 306 of the main barrier 302.

FIG. 10B illustrates the modular barrier device 300 as applied to skin (not shown) with adhesive 318. The main barrier 302 includes a main base surface 314 that is shown to be disposed on the skin without adhesive; however, adhesive can be applied to the main base surface 314. The perimeter device 304 includes a perimeter base surface 316 which is shown to be affixed to the skin with adhesive 318. The adhesive 318 is shown to be on the perimeter base surface 316, outer perimeter surface 308 and over the gap 311.

FIG. 10C illustrates the modular barrier device 300 being removed from the skin. As shown, the wire 312 is pulled from the wire recess 320 so as to cut, disrupt, separate, or otherwise remove the adhesive 318 from the device 300. This includes cutting the adhesive 318 adjacent to the wire recess 320 and/or gap 311 so that main barrier 302 can be separated from the perimeter barrier 304 and pulled from the skin.

Figure 11A:
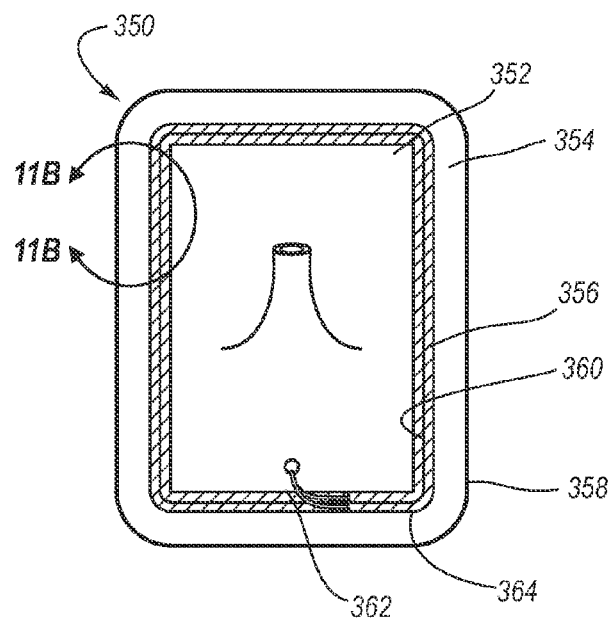
FIGS. 11A-11C include various views of an embodiment of a modular barrier device that includes decouplable members that can be separated from each other.
Figure 11B:
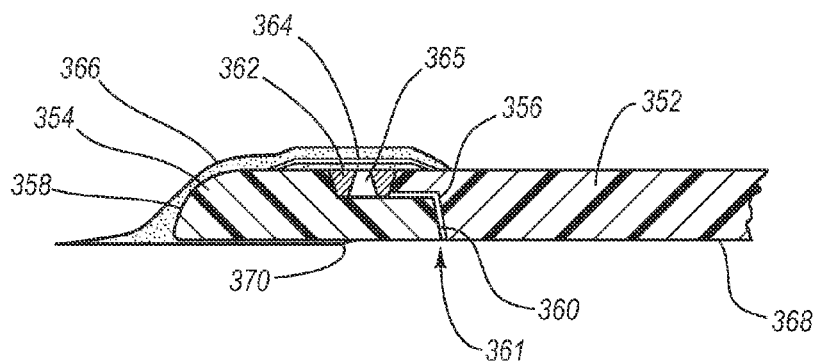
Figure 11C:
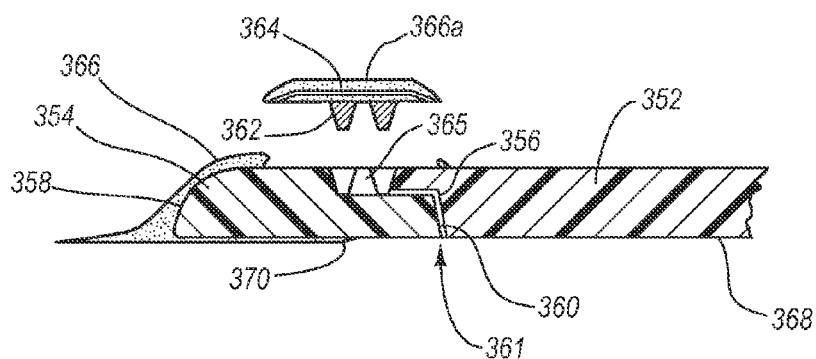

FIGS. 11A-11C illustrate another embodiment of a modular barrier device 350. The modular barrier device 350 can include a main barrier 352 and a perimeter barrier 354. The main barrier 352 can be configured as any barrier device as described herein. The perimeter barrier 354 is sized so as to be coupled/couplable to the perimeter surface 356 of the main barrier 352. For example, the perimeter barrier 354 can include an outer perimeter surface 358 and an inner perimeter surface 360 that is shaped and sized to conform with the perimeter surface 356 of the main barrier 352. When the main barrier 352 and perimeter barrier 354 are placed together so as to form the modular barrier device 350, the perimeter surface 356 forms a gap 361 with the inner perimeter surface 360 of the perimeter barrier 354. A release member 362, such as a wire, membrane, zip-lock members, or the like, can be imbedded on, within, at, or adjacent to the gap 361, such that pulling the release member 362 allows for the main barrier 352 to be decoupled from the perimeter barrier 354. As shown, the release member 362 is disposed within a junction 365 that extends around inner perimeter surface 360 of the perimeter barrier 354; however, the release member 362 and junction 365 can be in or at the gap 361 as well as within the main barrier 352 proximal or adjacent to the perimeter surface 356 of the main barrier 352. A cover member 364 can be disposed over or integrated with the release member 362 and junction 365 so as to keep the release member 360 disposed at the junction 365. The cover member 364 can be a material that is slit, cut, removed, lifted, or otherwise compromised such that pulling the release member 362 removes the cover member 364 and exposes junction 365 and gap 361. As shown, the cover member 364 is disposed over the perimeter surface 356 of the main barrier and inner perimeter surface 360 of the perimeter barrier 354.

FIG. 11B illustrates the modular barrier device 350 as applied to skin (not shown) with adhesive 366. The main barrier 352 includes a main base surface 368 that is shown to be disposed on the skin without adhesive; however, adhesive can be applied to the main base surface 368. The perimeter device 354 includes a perimeter base surface 370 which is shown to be affixed to the skin with adhesive 366. The adhesive 366 is shown to be on the perimeter base surface 370, outer perimeter surface 358 and over the gap 361.

FIG. 11C illustrates the modular barrier device 350 being removed from the skin. As shown, the release member 362 is pulled from the junction 365 so as to lift/detach the cover member 364 from the main barrier 352 and perimeter barrier 354 so as to cut, disrupt, separate, or otherwise remove the adhesive 366 from the device 350. This can expose the junction 365 and/or gap 311 so that main barrier 302 can be separated from the perimeter barrier 304 and pulled from the skin. For example, the release member can be configured similar to a zip lock, or releaseable cellophane membrane.

Figure 12A:
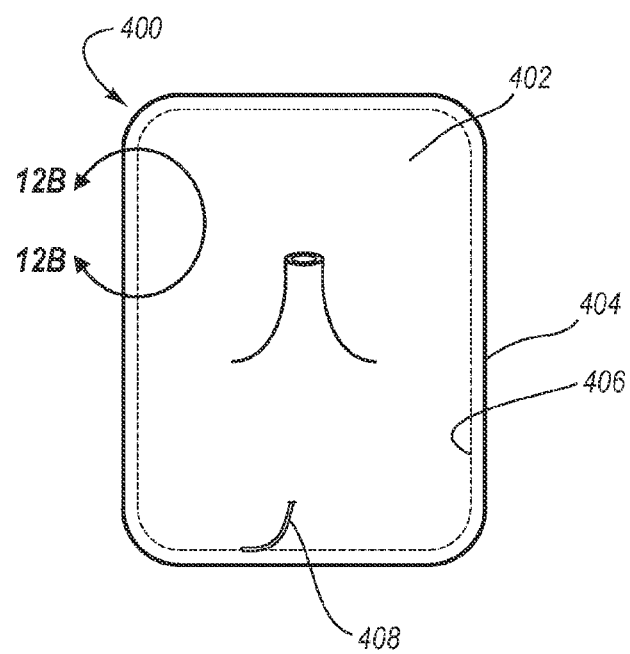
FIGS. 12A-12C include various views of an embodiment of a modular barrier device that includes decouplable members that can be separated by separation of a perforation.
Figure 12B:
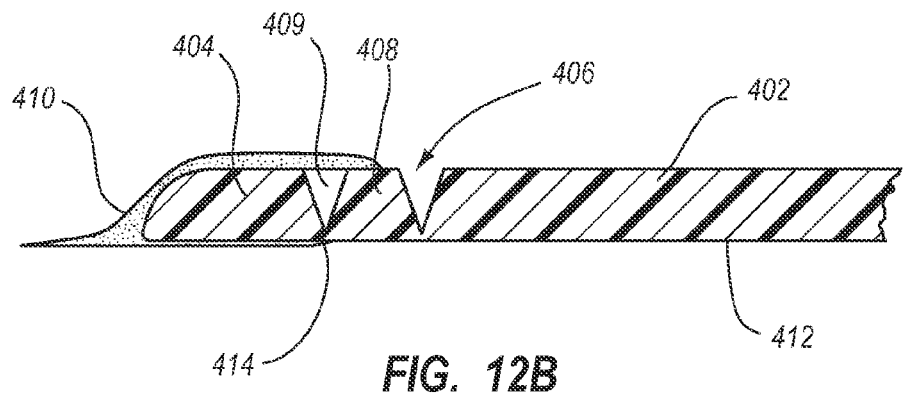
Figure 12C:
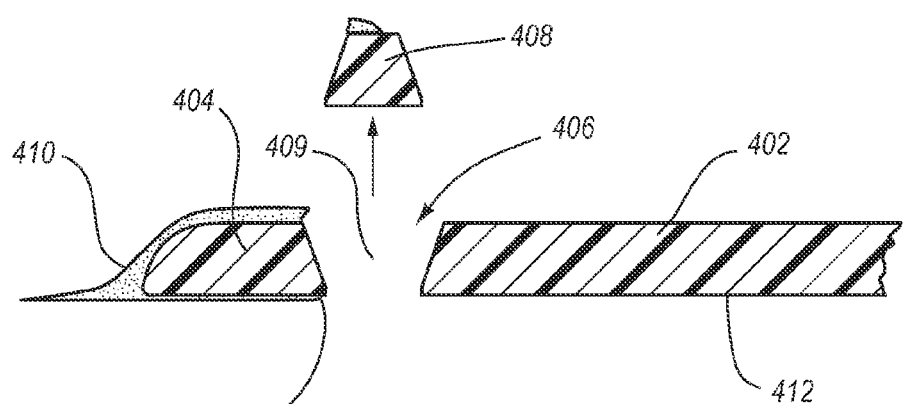

FIGS. 12A-12C illustrate an embodiment of a perforated barrier device 400. The perforated barrier device 400 has a perforation 406 that can be used to separate the main barrier 402 from a perimeter portion 404. The perforated barrier device 400 optionally may includes a rip member 408 that can be pulled to separate the main barrier 402 from the perimeter portion 404. The rip member 408 can be member that is pulled to split the perforation 406 or it can be an integrated member that separates at the perforation 406 when it is pulled from the device 400. Rip members 408 and perforation 406 are often found in food storage bags where the member can be ripped to open the bag.

FIG. 12B illustrates the perforated barrier device 400 as applied to skin (not shown) with adhesive 410. The main barrier 402 includes a main base surface 412 that is shown to be disposed on the skin without adhesive; however, adhesive can be applied to the main base surface 412. The perimeter portion 404 includes a perimeter base surface 414 which is shown to be affixed to the skin with adhesive 410. The perforation 406 is shown to include a rip member 408 that is coupled to the main barrier 402 and perimeter portion 404 such that removal or ripping of the rip member 408 opens the perforation 406. The perforation 406 also includes a plurality of perforation recesses 409 that allow for the rip member 408 to be easily removed. The perforation recesses 409 can be holes or any other perforation configuration.

In one embodiment, the barrier devices as described herein can be prepared as a series of nested barrier devices. This can include more than one barrier device being used in a series. Also, when configured as nested barrier devices, an antimicrobial composition can be disposed between the nested barrier devices or on any surface of the nested barrier devices.

The barrier devices as shown and described herein can include various features or configurations of any of the other barrier devices. As such, a feature or configuration of one depicted barrier device can be included on another embodiment of a barrier device that is shown in a different figures. Thus, the features of the barrier devices are interchangeable and can be used together as desired.

II. Adhesive

As described, the barrier device can be utilized with an adhesive in order to provide the static or stable retention of the medical device with respect to the incision as well as the inhibition or prevention of infections from entering the incision. A variety of adhesives can be used, such as those that are compatible with the skin that do not cause serious skin irritation. Also, the adhesive can be compatible with the barrier device and medical device so as to promote adhesion with limited damage or degradation of the structural integrity thereof.

In one embodiment, the bioadhesive is any biocompatible adhesive. As such, reference to a bioadhesive herein is a natural or synthetic substance that adheres to skin without substantial side effects or complications. Examples of such biocompatible adhesives (bioadhesives) are substantially non-toxic, non-inflammatory, and configured to adhere to the body of a medical device and to skin. These types of adhesives, contact adhesives, are commonly used in transdermal drug delivery devices. Also, these types of adhesives are well known to those of ordinary skill in the relevant arts.

In one embodiment, the bioadhesive is a polymer or monomer that polymerizes into a polymer that is configured to adhere to skin and to the body of a medical device. For example, the polymer is biocompatible and flexible. This allows for being directly applied to the skin at a site of insertion of a medical device, and allows the medical device the ability to move with respect to the insertion site without breaking the adhesive bond.

In one embodiment, the bioadhesive is comprised of silicones, vinyls, polyethylenes, polyvinylchlorides, polyacrylates, polymethacrylates, polyisobutylenes, monomers thereof that form adhesive, and the like which are biocompatible.

In one embodiment, the bioadhesive is comprised of serum albumin and glutaraldehyde, such as BioGlue™.

In one embodiment, the bioadhesive is a composition that includes a cyanoacrylate. Cyanoacrylates are compounds commonly used in the adhesive industry. For example, the cyanoacrylate can include a methyl-2-cyanoacrylate ethyl-2-cyanoacrylate (i.e., Superglue™ and Krazy Glue™), and 2-octyl cyanoacrylate or n-butyl-cyanoacrylate, which are used in medical glues (i.e., Dermabond™ and Traumaseal™), a polyacrylate, polycyanoacrylate, other cyanoacrylates, and combinations thereof. Cyanoacrylate is a tenacious adhesive, particularly when used to bond skin with a medical device, where the skin usually has minute traces of water. In its liquid form, cyanoacrylate consists of monomers of cyanoacrylate molecules. Methyl-2-cyanoacrylate ($CH_2$=$C(CN)COOCH_3$ or $C_5H_5NO_2$) has a molecular weight equal to 111.1, a flashpoint of 79° C., and 1.1 times the density of water. Ethyl-2-cyanoacrylate ($C_6H_7NO_2$) has a molecular weight equal to 125 and a flashpoint of >75° C. Also, the cyanoacrylates are susceptible to fracture and loss of adhesiveness when chilled to an appropriate temperature, which allows for the use of chilling in order to remove the barrier device from the skin of a subject.

Generally, a cyanoacrylate is an acrylic resin which rapidly polymerizes in the presence of water, forming long, strong chains, joining the bonded surfaces together. Because the presence of moisture causes the glue to set, exposure to moisture in the air can cause a tube or bottle of glue to become unusable over time. To prevent an opened container of glue from setting before use, it should be stored in an airtight jar or bottle, and optionally with a package of silica gel.

Another important trait is that cyanoacrylate sets quickly, often in less than a minute. A normal bond reaches full strength in two hours and is waterproof. Accelerators such as toluidine trigger setting in two or three seconds, with some loss of strength.

The adhesive can be configured so as to produce and maintain strong glue-skin, glue-barrier device, and glue-catheter adhesive interfaces. Such strong adhesive interfaces have been shown by adhering materials (e.g., polyurethanes, polyethylenes, polypropylenes, PVC, Teflon, and the like) that can be used in the barrier device and medical device to skin with an adhesive in accordance with the present invention. Thus, the adhesive and/or device of the present invention could be used as an antimicrobial barrier for most central venous catheter sites of insertion, as well as other sites of insertions for other medical devices.

Alternatively, the cyanoacrylate can be substituted by another bioadhesive that is configured to adhere to skin and to the body of a medical device, such as a catheter. This is because certain polymers, which are bioadhesive, can create an occlusive barrier between the skin and a medical device, wherein the occlusive barrier is resistant to penetration by bacteria or other microbes. Applying these polymers at the site of catheter entry or entry of other medical device through the skin prevent catheter-related infections by inhibiting microbes from entering into the site of entry and colonizing at the percutaneous site and/or on the catheter portion that is disposed within the skin.

Experiments can be utilized to determine whether a bioadhesive is suitable for the present invention. Suitable bioadhesives can be applied to the skin and medical device at the site of insertion to form a barrier. The barrier can be visually inspected to insure the barrier is sufficient. For example, a histologic cross-section can be studied to ensure the bioadhesive is sufficient. Additionally, the barrier can be examined for barrier function by examining the movement of bacteria after being placed over the intact barrier, and evaluating for penetrance of those bacteria beyond that barrier.

In one embodiment, one or more different types of adhesives can be used at various locations of the barrier device, skin, and/or medical device. This can include one type of adhesive for the base surface and a different adhesive for the perimeter. For example, a weaker adhesive can be used on the base while a stronger adhesive can be used at the perimeter.

In one embodiment, the base surface can include a peelable liner that protects an adhesive composition disposed on the base surface such that the base surface can be adhered to the skin after the peelable liner is removed. The adhesive on the base surface under the peelable liner can be any type of adhesive, such as pressure adhesives and those adhesives used in transdermal devices. Thus, the base of the barrier device can be applied to the skin similarly to a transdermal device. Moreover, a drug can be included in the adhesive on the base surface so that the barrier device can be used as a transdermal drug delivery device. This can include the use of anesthetics, antimicrobials, or the like being delivered to the skin under the barrier device.

III. Kit

In one embodiment, the present invention includes a catheter kit that has a barrier device and adhesive, such as a cyanoacrylate, as described herein. The barrier device and/or adhesive can be configured to be placed at the catheter insertion site as described so as to form a barrier with the skin and catheter so that microbes are inhibited from entering the insertion site. For example, the anti-microbial barrier formed from the barrier device and adhesive can be maintained when used on a percutaneously placed central venous catheter.

In one embodiment, the present invention includes a includes an adhesive (e.g., cyanoacrylate) and barrier device that can be used together to form an anti-microbial barrier for an opening in skin where a medical device extends through. For example, the cyanoacrylate composition and/or device can be used as a mechanical and/or therapeutic barrier that has antimicrobial properties. That is, the cyanoacrylate composition and/or device can physically prevent microbes from entering a medical device insertion site and can effect antimicrobial properties.

IV. Application

In one embodiment, the present invention includes a method of using a barrier device in combination with an adhesive, such as those that contain a cyanoacrylate, in order to form an impermeable barrier against bacteria at a percutaneous incision site for passing a medical device into or through skin. As such, the device and adhesive are placed at the incision so as to contact the skin and barrier device so as to form a barrier. Also, the adhesive can be used to form barriers between the barrier device and medical device as well as between the skin and medical device in order to provide one or more barriers as described. The one or more barriers can retain the medical device in a static position relative to the skin and incision such that a barrier inhibits bacteria from entering the incision. Bacteria tend to infect catheters by contaminating the catheter at the site of the percutaneous incision and subsequently traveling down the external surface of the catheter and into the bloodstream. Thus, the one or more barriers formed with the barrier device and adhesive can both provide a static medical device position as well as provide a barrier that inhibits microbial infections in the incision.

In one embodiment, the barrier is formed from a flowable adhesive composition that hardens at a skin-barrier device interface, skin-medical device interface, and/or barrier device-medical device interface. Such flowable adhesive compositions can be liquids, gels, pastes, and the like. The flowable composition can be placed onto the skin, barrier device, and medical device at an interface therebetween, which is usually at, adjacent, or proximal with the percutaneous incision. For example, an adhesive composition can be administered onto the skin adjacent to a percutaneously inserted intravascular catheter and the barrier device can be applied to the adhesive so as to receive the catheter therein so as to reduce the risk of developing a catheter-related infection. In another example, a fluid (e.g., liquid or paste) adhesive is applied to the intersection between the skin and the perimeter of the barrier device so as to create a perimeter barrier therearound. In yet another example, the adhesive is applied to a medical device disposed in an incision, and the barrier device is slid or applied over the medical device so as to come into contact with the skin so that a barrier forms between the medical device and barrier device (and optionally to the skin) in the barrier device conduit. In still yet another example, adhesive is applied to the barrier device at the top opening from with the medical device protrudes to form a barrier with the medical device. In another example, adhesive is applied to a clam-type barrier device that is then closed around the medical device and adhered to the skin. In yet another example, adhesive is applied to a groove and base surface of a barrier device and then the barrier device is applied to the medical device and skin such that the medical device is adhered to the groove and the base surface is adhered to the skin. Other methods of use are also contemplated.

In one embodiment, the barrier device and adhesive can be used to inhibit or prevent pistoning of the catheter within the incision. Pistoning can include slight movements, in and out, of the catheter that can introduce bacteria into the incision and catheter tract. Sutures have been found to be insufficient to prevent pistoning; however, the use of the barrier device and adhesive can effectively inhibit pistoning. Additionally, sutures form additional holes in the skin which themselves can lead to infection. The barrier device of the present invention can be used to inhibit slight pistoning. This can include inhibiting pistoning that moves the medical device from about 0.5 mm to about 10 mm into or out of the incision, from about 1 mm to about 5 mm, or about 2 mm to about 3 mm movements can be prevented. This can prevent infectious material from being introduced into the catheter line or other incision having a percutaneous medical device.

While some pistoning may occur during use of the device, the sterile environment around the incision and proximal portions of the medical device provided by the barrier device can be maintained so that infections are not introduced into the incision. As such, the barrier device maintains sterility of the incision as proximal areas by virtue of the barriers that are formed by the barrier device and adhesive combination. Accordingly, minor pistoning may occur, but substantially no microbes will be able to enter into and infect the incision.

In one embodiment, the present invention includes a method for removing the adhesive-formed barrier and barrier device from the skin around or adjacent to the incision site between the skin and medical device. Such a method can include applying a solvent to the adhesive so as to degrade the adhesive so that the barrier device can be removed from the skin. Solvents such as acetone or tetrahydrofuran, and the like can be used to soften the cyanoacrylate adhesive. Solvents that soften through dissolve the adhesives of the present invention are well known in the art.

Additionally, the adhesive can be cooled so as to cause the bond between the skin, barrier device, and/or medical device to become brittle. This can be accomplished by locally decreasing the temperature with a coolant, such as liquid nitrogen or other cooling fluid. For example, the cooling fluid can be applied to the external surfaces of the adhesive or through conduits to internal surfaces of the adhesive. When the adhesive cools sufficiently, it can be easily cracked or broken in order to remove the barrier device.

Also, an inflatable bladder can be disposed between the barrier device and adhesive such that inflation of the bladder causes the adhesive barrier to break. This inflatable bladder can then be used to separate the bond between the skin and the medical device and/or barrier device so that the medical device and/or barrier device can be removed from the skin. Thus, the bladder can use hydraulic pressure and thereby expand so as to mechanically break the bond of the barrier.

Additionally, a release cord could be used in order to break the barrier between the barrier device and skin. For example, a release cord attached to the barrier device can be pulled so that it cuts the adhesive barrier and separates the barrier device from the skin. Such a release cord can also separate the barrier device from the medical device.

Of course, the skin, barrier device, and medical device can be sterile during the use described herein. Also, the procedures described can be performed in a manner that does not introduce or propagate infections. Additionally, sterilization techniques can be conducted to sterilize the skin, barrier device, and medical device before, during, and/or after placement of the catheter into an incision as well as placement of the barrier device with respect to the medical device and skin.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references (e.g., journal articles, published patent applications, patents, websites, and the like) that are recited herein are incorporated herein by specific reference in their entirety.

The invention claimed is:

1. A barrier system for reducing infections associated with a percutaneous medical device, said barrier system comprising:
    a barrier device having a skin-contacting surface with an adhesive-receiving surface and a percutaneous medical device-receiving surface;
    one or more of an expandable bladder or release cord for releasing the barrier device from skin associated with the skin-contacting surface, the expandable bladder is disposed on the barrier device, or the release cord is disposed on the skin-contacting surface of the barrier device; and
    a cyanoacrylate adhesive composition configured for adhering to skin, the barrier device, the one or more of an expandable bladder or release cord, and/or the percutaneous medical device so as to form an antimicrobial barrier at or adjacent to an incision in the skin where the percutaneous medical device is percutaneously inserted through the skin, and wherein the one or more of an expandable bladder or release cord is capable of breaking a cyanoacrylate adhesive-skin bond.

2. The barrier system as in claim 1, wherein the barrier device includes a conduit configured to receive the percutaneous medical device.

3. The barrier system as in claim 2, wherein the barrier device includes a base surface having a base opening that is in fluid communication with the conduit and an opposite surface having an opposite opening that is in fluid communication with the base opening via the conduit.

4. The barrier system as in claim 3, wherein the conduit is substantially orthogonal with the base surface.

5. The barrier system as in claim 3, wherein the conduit is at an angle from about 0 degrees to about 90 degrees with respect to the base surface.

6. The barrier system as in claim 1, wherein the cyanoacrylate is selected from the group consisting of methyl-2-cyanoacrylate, 2-octyl cyanoacrylate, and n-butyl-cyanoacrylate.

7. The barrier system as in claim 1, wherein the barrier device includes a groove in a base surface that is configured to receive the percutaneous medical device.

8. The barrier system as in claim 1, further comprising at least one of the following:
    a fastener disposed on the barrier device that is configured for receiving the percutaneous medical device;
    one or more fastener straps on the barrier device that is configured to be affixed to the skin outward from the barrier device;
    a tapered base opening or opposite opening;
    a uniform conduit cross-sectional profile;
    a tapered conduit cross-sectional profile;
    a recess in the conduit configured for receiving the adhesive;
    a recess in the base surface configured for receiving the adhesive;
    a groove adjacent with the opposite opening;
    an O-ring; or
    a chilling fluid conduit in the barrier device that communicates with a location for receiving the adhesive.

9. A barrier system as in claim 1, wherein the barrier device is disposed on the skin with the adhesive and the one or more of an expandable bladder or release cord therebetween so as to receive the percutaneous medical device protruding from the incision.

10. A catheter system for reducing infections associated with catheters, said catheter system comprising:
    a catheter medical device;
    a barrier device having a skin-contacting surface with an adhesive-receiving surface and a catheter-receiving surface;
    one or more of an expandable bladder or release cord for releasing the barrier device from skin associated with the skin-contacting surface, the expandable bladder is disposed on the barrier device, or the release cord is disposed at least partially in contact with the adhesive composition; and
    a cyanoacrylate adhesive composition configured for adhering to skin, the barrier device, the one or more of an expandable bladder or release cord, and/or the catheter so as to form a barrier at or adjacent to an incision in the skin where the catheter is percutaneously inserted through the skin, and wherein the one or more of an expandable bladder or release cord is capable of breaking a cyanoacrylate adhesive-skin bond.

11. The catheter system as in claim 10, wherein barrier device includes a conduit configured to receive the catheter.

12. The catheter system as in claim 11, wherein the barrier device includes a base surface having a base opening that is in fluid communication with the conduit and an opposite surface having an opposite opening that is in fluid communication with the base opening via the conduit.

13. The catheter system as in claim 12, wherein the conduit is substantially orthogonal with the base surface.

14. The catheter system as in claim 12, wherein the conduit is at an angle from about 0 degrees to about 90 degrees with respect to the base surface.

15. The catheter system as in claim 10, wherein the cyanoacrylate is selected from the group consisting of methyl-2-cyanoacrylate, 2-octyl cyanoacrylate, and n-butyl-cyanoacrylate.

16. The catheter system as in claim 10, wherein the barrier device includes a groove in a base surface that is configured to receive the catheter.

17. The catheter system as in claim 10, further comprising at least one of the following:
- a fastener disposed on the barrier device that is configured for receiving the catheter;
- one or more fastener straps on the barrier device that is configured to be affixed to the skin outward from the barrier device;
- a tapered base opening or opposite opening;
- a uniform conduit cross-sectional profile;
- a tapered conduit cross-sectional profile;
- a recess in the conduit configured for receiving the adhesive;
- a recess in the base surface configured for receiving the adhesive;
- a groove adjacent with the opposite opening;
- an O-ring;
- a chilling fluid conduit in the barrier device that communicates with a location for receiving the adhesive;
- a secondary conduit lined with another material; or
- a secondary conduit filled with another material.

18. A catheter system as in claim 10, wherein the barrier device is disposed on the skin with the adhesive and release member therebetween so as to receive the catheter protruding from the incision.

19. A method for reducing infections associated with percutaneous medical devices, said method comprising:
- inserting, percutaneously, a medical device into skin of a subject;
- applying a cyanoacrylate adhesive composition to the skin and/or the adhesive-receiving surface of a barrier device having a skin-contacting surface with an adhesive-receiving surface, a percutaneous medical device-receiving surface and one or more of an expandable bladder or release cord, wherein the adhesive receiving surface of the barrier device is separate from the percutaneous medical device-receiving surface such that the adhesive does not simultaneously contact the skin and medical device;
- adhering the barrier device to the skin with the cyanoacrylate adhesive composition so as to form an anti-microbial barrier spaced apart from the medical device with respect to the incision and the barrier device, the one or more of an expandable bladder or release cord, and/or the percutaneous medical device medical device to inhibits microbes from infecting the incision, and
- breaking a cyanoacrylate adhesive-skin bond by expanding the one or more expandable bladder or pulling the release cord.

20. A method as in claim 19, wherein the adhesive is applied to at least one of the following:
- a junction between the barrier device and skin;
- a junction between the barrier device, skin, and air;
- a junction between the barrier device and medical device; or
- a junction between the barrier device, medical device, and air.

21. A method as in claim 20, wherein the medical device is inhibited from pistoning within the incision.

22. A method as in claim 20, wherein the medical is inhibited from pistoning more than about 2 mm to about 3 mm within the incision.

23. A method as in claim 20, wherein a sterile environment is maintained in and/or proximal to the incision site in the skin while the percutaneous medical device is disposed therein.

24. A method as in claim 19, further comprising applying the cyanoacrylate adhesive composition to the medical device so as to adhere the medical device to the barrier device so as to form an anti-microbial barrier that inhibits microbes from infecting the incision.

25. A method as in claim 19, further comprising applying the cyanoacrylate adhesive onto at least one of the skin-contacting surface or medical device-contacting surface of the barrier device.

* * * * *